(12) United States Patent
Yamamoto

(10) Patent No.: US 10,702,136 B2
(45) Date of Patent: Jul. 7, 2020

(54) ENDOSCOPE SYSTEM, PROCESSOR DEVICE, AND METHOD FOR OPERATING ENDOSCOPE SYSTEM

(71) Applicant: FUJIFILM Corporation, Tokyo (JP)

(72) Inventor: Hiroaki Yamamoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/535,578

(22) Filed: Aug. 8, 2019

(65) Prior Publication Data
US 2019/0357759 A1 Nov. 28, 2019

Related U.S. Application Data

(63) Continuation of application No. PCT/JP2017/046364, filed on Dec. 25, 2017.

(30) Foreign Application Priority Data

Mar. 3, 2017 (JP) .................................. 2017-040342

(51) Int. Cl.
*A61B 1/045* (2006.01)
*A61B 1/00* (2006.01)
(Continued)

(52) U.S. Cl.
CPC .............. *A61B 1/045* (2013.01); *A61B 1/005* (2013.01); *A61B 1/00009* (2013.01);
(Continued)

(58) Field of Classification Search
USPC ........................................... 382/128; 348/45
See application file for complete search history.

(56) References Cited

U.S. PATENT DOCUMENTS 7,459,696 B2 * 12/2008 Schomacker ........ A61B 5/0059
250/458.1
9,916,666 B2 * 3/2018 Kanda ................ A61B 1/00009
(Continued)

FOREIGN PATENT DOCUMENTS

EP  2 859 833 A1  4/2015
EP  3 005 933 A1  4/2018
(Continued)

OTHER PUBLICATIONS

International Preliminary Report on Patentability and English translation of the Written Opinion of the International Searching Authority (Forms PCT/IB/326, PCT/IB/373, and PCT/ISA/237) for International Application No. PCT/JP2017/046364, dated Sep. 12, 2019.
(Continued)

*Primary Examiner* — Ishrat I Sherali
(74) *Attorney, Agent, or Firm* — Birch, Stewart, Kolasch & Birch, LLP

(57) ABSTRACT

An endoscope system 10 includes: an image acquiring unit 54 that acquires an endoscope image obtained by imaging an observation target; a baseline information calculating unit 82 that calculates baseline information (operation value "Z") by using the endoscope image, the baseline information being information about light scattering characteristics or light absorbing characteristics of the observation target and information that is at least not dependent on particular biological information; a region setting unit 83 that sets, by using the baseline information, a calculation region in which the index value is to be calculated, the index value indicating a state of the observation target; and an index value calculating unit 84 that calculates the index value in the calculation region set by the region setting unit 83, by using the endoscope image.

20 Claims, 6 Drawing Sheets

(51) Int. Cl.
*A61B 1/005* (2006.01)
*A61B 1/06* (2006.01)
*G02B 23/24* (2006.01)

(52) U.S. Cl.
CPC ........ *A61B 1/0638* (2013.01); *G02B 23/2461* (2013.01); *A61B 1/00006* (2013.01); *A61B 1/0676* (2013.01)

(56) References Cited

U.S. PATENT DOCUMENTS

| | | | |
|---|---|---|---|
| 2009/0322863 A1* | 12/2009 | Takahashi | G01C 3/00 348/65 |
| 2011/0230715 A1 | 9/2011 | Saito | |
| 2013/0051680 A1 | 2/2013 | Kono et al. | |
| 2015/0092993 A1 | 4/2015 | Kanda et al. | |
| 2017/0112357 A1 | 4/2017 | Kono et al. | |
| 2018/0218233 A1* | 8/2018 | Yamanashi | G02B 23/24 |
| 2019/0069768 A1* | 3/2019 | Chiba | A61B 1/00 |
| 2019/0192048 A1* | 6/2019 | Makino | A61B 5/00 |

FOREIGN PATENT DOCUMENTS

| | | |
|---|---|---|
| EP | 3 427 637 A1 | 1/2019 |
| JP | 2011-194028 A | 10/2011 |
| JP | 2013-51987 A | 3/2013 |
| JP | 2013-255656 A | 12/2013 |
| WO | WO 2016/009861 A1 | 1/2016 |

OTHER PUBLICATIONS

International Search Report (Form PCT/ISA/210) for International Application No. PCT/JP2017/046364, dated Jan. 30, 2018, with English translation.

Extended European Search Report dated Feb. 7, 2020, for corresponding European Application No. 17898401.9.

\* cited by examiner

ENDOSCOPE SYSTEM, PROCESSOR DEVICE, AND METHOD FOR OPERATING ENDOSCOPE SYSTEM

CROSS-REFERENCE TO RELATED APPLICATIONS

This application is a Continuation of PCT International Application No. PCT/JP2017/046364 filed on Dec. 25, 2017, which claims priority under 35 U.S.C. § 119(a) to Japanese Patent Application No. 2017-040342 filed on Mar. 3, 2017. Each of the above application(s) is hereby expressly incorporated by reference, in its entirety, into the present application.

BACKGROUND OF THE INVENTION

1. Field of the Invention

The present invention relates to an endoscope system that calculates an index or the like to be used for diagnosis, a processor device, and a method for operating the endoscope system.

2. Description of the Related Art

In the medical field, an endoscope system including a light source device, an endoscope, and a processor device is widely used. In particular, in recent years, the following endoscope system has been known. The endoscope system not only images an observation target by using the endoscope but also calculates information, an index, or the like (hereinafter these are collectively called an index value) that indicates the state of the observation target that is difficult to know at a sight, such as an oxygen saturation, by using an image obtained by imaging the observation target.

When calculating the index value, in a case where the state of the observation target is not suitable for calculating the index value, such as the state where a residue or a residual liquid (hereinafter referred to as a residual liquid or the like) is attached to the observation target, an inaccurate index value may be calculated. Thus, for example, in an endoscope system of the related art that calculates the index value, the observed part or the influence of the residual liquid is corrected (JP2011-194028A). In addition, an endoscope system that identifies a region where the residual liquid or the like is present and excludes it from the inspection target is also known (JP2013-051987A).

SUMMARY OF THE INVENTION

In a case of calculating the index value as described above, a region that is not suitable for calculating the index value has been attempted to be excluded from a target for calculating the index value in the related art. However, it is still not easy to accurately exclude a part in which the index value cannot be accurately calculated from an endoscope image. For example, as described above, since the index value becomes an inaccurate value in a region to which the residual liquid or the like is attached, exclusion of the part to which the residual liquid or the like is attached from the target for calculating the index value is effective in increasing the reliability of the calculated index value. However, if only the region to which the residual liquid or the like is attached is excluded, an accurate index value cannot be calculated in the other regions. Specifically, the calculation accuracy of the index value is typically dependent on, not only the presence or absence of the residual liquid or the like, but also light scattering characteristics or light absorbing characteristics of the observation target. Thus, in a region in which the observation target actually has unexpected light scattering characteristics or light absorbing characteristics or, for example, in a region in which the observation target seems to have the unexpected light scattering characteristics or light absorbing characteristics due to the way of irradiation with the illumination light or the like, the accurate index value cannot be calculated in some cases even if the residual liquid or the like is not present.

An object of the present invention is to provide an endoscope system, a processor device, and a method for operating the endoscope system that can identify, more easily and more accurately than in the related art, the region in which the index value cannot be accurately calculated and the region in which the index value can be accurately calculated.

An endoscope system according to the present invention is an endoscope system including a light source, an endoscope, and a processor device, the endoscope imaging an observation target irradiated with light emitted from the light source, the processor device performing system control and image processing. The endoscope system includes: an image acquiring unit that acquires an endoscope image obtained by imaging the observation target; a baseline information calculating unit that calculates baseline information by using the endoscope image or a display endoscope image generated by using the endoscope image, the baseline information being information about light scattering characteristics or light absorbing characteristics of the observation target and information that is at least not dependent on particular biological information; a region setting unit that sets, by using the baseline information, a calculation region in which an index value is to be calculated, the index value indicating a state of the observation target; and an index value calculating unit that calculates the index value in the calculation region set by the region setting unit, by using the endoscope image or the display endoscope image generated by using the endoscope image.

The baseline information calculating unit preferably calculates the baseline information for each part composed of one or more pixels of the endoscope image, and the region setting unit preferably determines whether the index value is to be calculated for the part to set a region formed of one or more of the parts as the calculation region in which the index value is to be calculated.

The region setting unit preferably sets the calculation region in which the index value is to be calculated, on the basis of a comparison result of comparison between the baseline information and a threshold value.

If a plurality of pieces of the baseline information are calculated, the region setting unit preferably sets the threshold value by using one piece of the baseline information among the plurality of pieces of the baseline information or a statistic calculated by using the plurality of pieces of the baseline information.

The region setting unit preferably excludes, by using the baseline information, any one or more of a region in which a residue or a residual liquid is present, a dark region, a halation region, or a region in which a treatment tool is present to set the calculation region in which the index value is to be calculated.

The baseline information calculating unit preferably calculates the baseline information by using a plurality of the endoscope images with different kinds of illumination light used for imaging.

The index value calculating unit preferably calculates the index value by using one or more of the endoscope images for which kinds of illumination light used for imaging are different from kinds of illumination light for a plurality of the endoscope images to be used for calculating the baseline information by the baseline information calculating unit.

It is preferable to include a display unit that displays the endoscope image or an image generated by using the endoscope image, and the index value.

It is preferable to include a display unit that displays the calculation region in which the index value is to be calculated in the endoscope image or the image generated by using the endoscope image.

The particular biological information is preferably information that changes due to a state of hemoglobin included in the observation target.

The particular biological information is preferably an oxygen saturation or a hemoglobin concentration.

The particular biological information is preferably information about a blood vessel included in the observation target.

The particular biological information is preferably a blood vessel density, a blood vessel depth, or a blood vessel thickness.

A processor device according to the present invention is a processor device that performs system control and image processing of an endoscope system having a light source and an endoscope that images an observation target irradiated with light emitted from the light source. The processor device includes: an image acquiring unit that acquires an endoscope image obtained by imaging the observation target; a baseline information calculating unit that calculates baseline information by using the endoscope image or a display endoscope image generated by using the endoscope image, the baseline information being information about light scattering characteristics or light absorbing characteristics of the observation target and information that is at least not dependent on particular biological information; a region setting unit that sets, by using the baseline information, a calculation region in which an index value is to be calculated, the index value indicating a state of the observation target; and an index value calculating unit that calculates the index value in the calculation region set by the region setting unit, by using the endoscope image or the display endoscope image generated by using the endoscope image.

A method for operating an endoscope system according to the present invention is a method for operating an endoscope system including a light source, an endoscope, and a processor device, the endoscope imaging an observation target irradiated with light emitted from the light source, the processor device performing system control and image processing. The method includes: a step of acquiring, by an image acquiring unit, an endoscope image obtained by imaging the observation target; a step of calculating, by a baseline information calculating unit, baseline information by using the endoscope image or a display endoscope image generated by using the endoscope image, the baseline information being information about light scattering characteristics or light absorbing characteristics of the observation target and information that is at least not dependent on particular biological information; a step of setting, by a region setting unit by using the baseline information, a calculation region in which an index value is to be calculated, the index value indicating a state of the observation target; and a step of calculating, by an index value calculating unit, the index value in the calculation region set by the region setting unit, by using the endoscope image or the display endoscope image generated by using the endoscope image.

According to the endoscope system, the processor device, and the method for operating the endoscope system according to the present invention, it is possible to identify, more easily and more accurately than in the related art, the region in which the index value cannot be accurately calculated and the region in which the index value can be accurately calculated.

DESCRIPTION OF THE PREFERRED EMBODIMENTS

Figure 1:
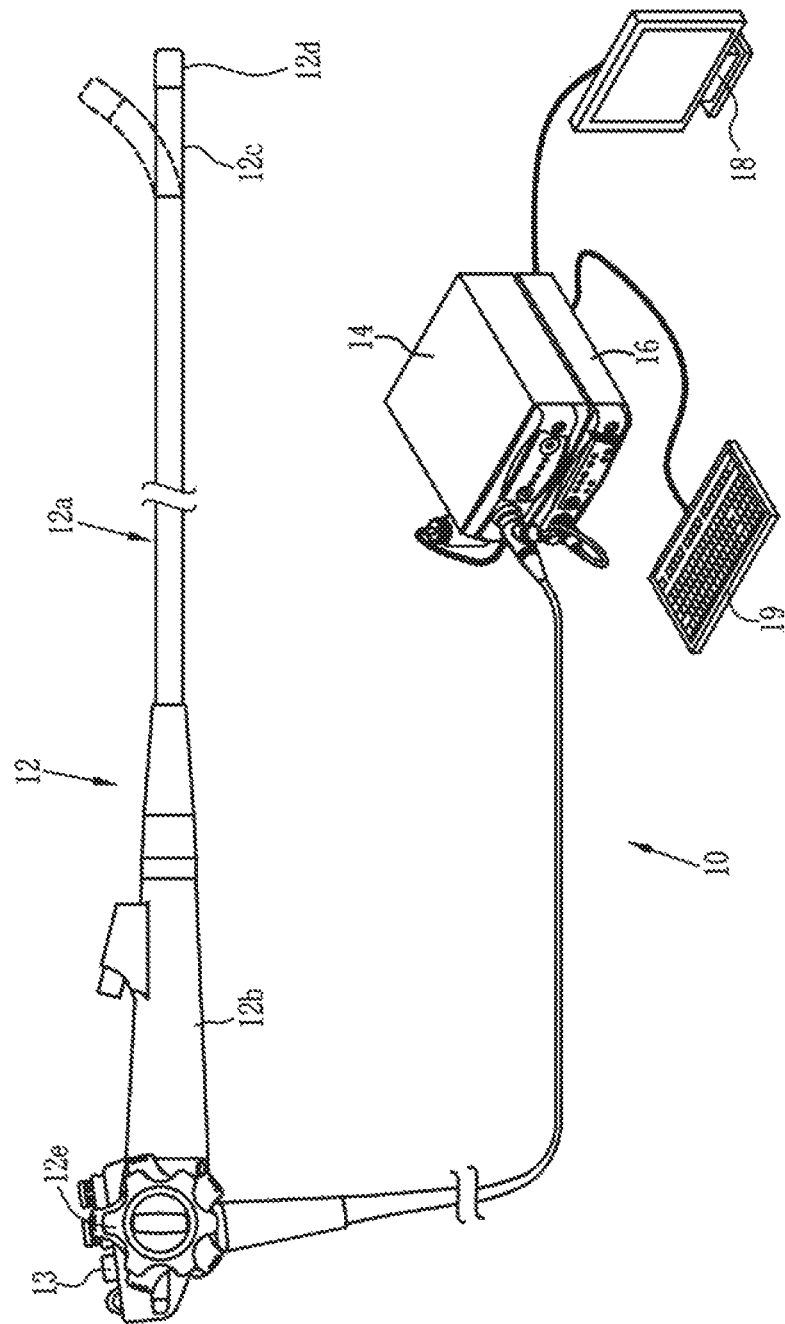
FIG. 1 is an external view of an endoscope system.

As illustrated in FIG. 1, an endoscope system 10 includes an endoscope 12, a light source device 14, a processor device 16, a monitor 18, and a console 19. The endoscope 12 images an observation target. The light source device 14 generates illumination light. The processor device 16 performs system control, image processing, and the like of the endoscope system 10. The monitor 18 is a display unit that displays a display endoscope image generated by the processor device 16. The console 19 is an input device used for inputting settings to the processor device 16, for example.

The endoscope 12 has an insertion part 12a that can be inserted into a subject, an operating unit 12b provided at the base end portion of the insertion part 12a, and a bending part 12c and a tip part 12d provided at the distal end side of the insertion part 12a. Operation of an angle knob 12e of the operating unit 12b causes the bending part 12c to bend. As a result of bending of the bending part 12c, the tip part 12d is oriented in a desired direction. Note that the tip part 12d is provided with an ejection port (not illustrated) through which air, water, or the like is ejected toward the observation target. In addition, the operating unit 12b is provided with a zoom operating unit 13 in addition to the angle knob 12e. Operation of the zoom operating unit 13 causes zoom in or zoom out of the observation target for imaging.

Figure 2:
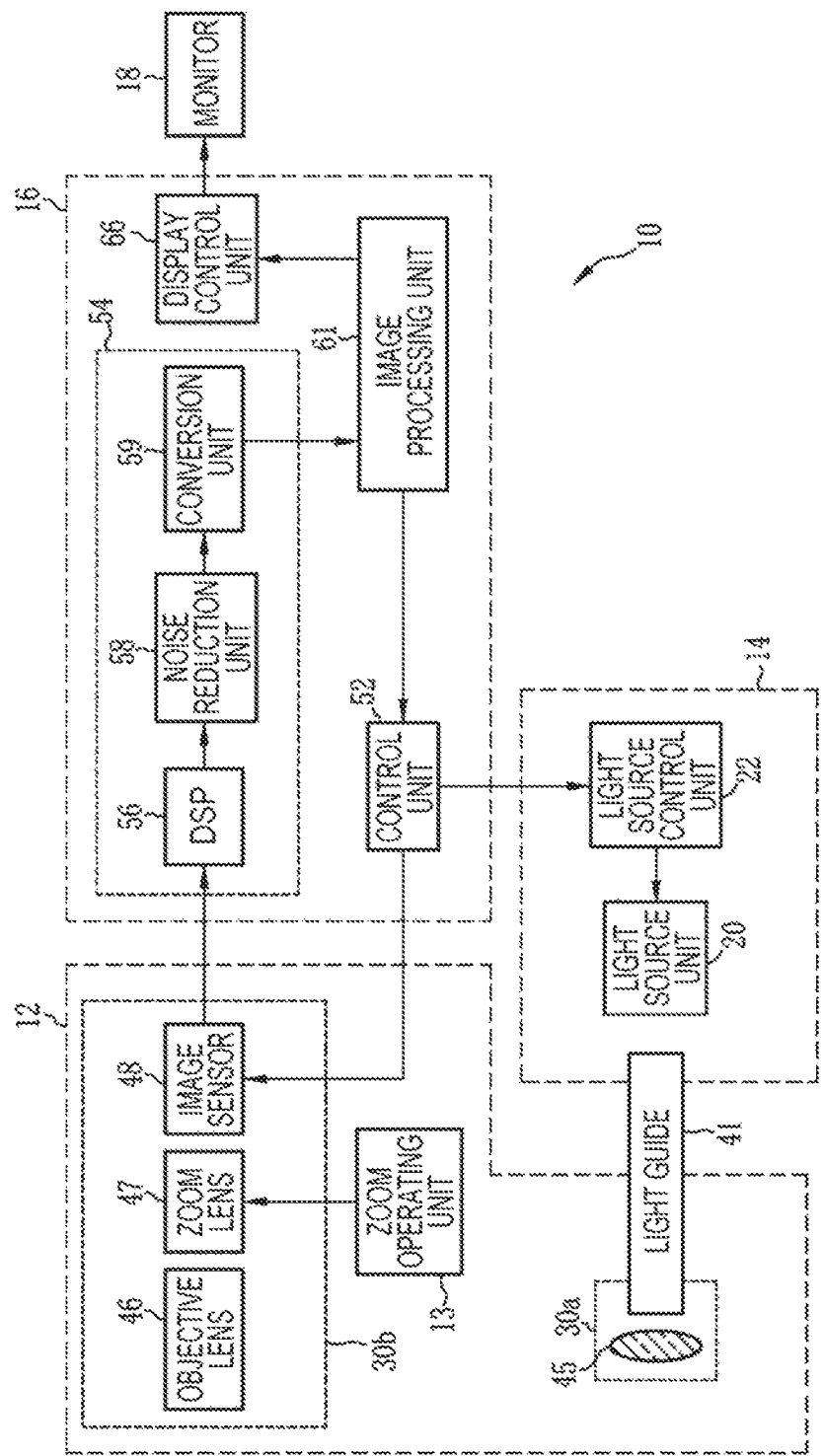
FIG. 2 is a block diagram of the endoscope system.

As illustrated in FIG. 2, the light source device 14 includes a light source unit 20 that emits illumination light and a light source control unit 22 that controls driving of the light source unit 20.

The light source unit 20 includes, for example, a plurality of light emitting diodes (LEDs) that emit light beams with different center wavelengths or wavelength ranges (hereinafter simply referred to as "different wavelengths") as a light source and can emit a plurality of kinds of illumination light with different wavelengths by light emission or turning on of the LEDs, adjustment of light amount, or the like. For example, the light source unit 20 can emit, as the illumination light, each of wide-band violet light, blue light, green light, and red light whose wavelength ranges are comparatively wide. In particular, in addition to the wide-band violet light, blue light, green light, and red light, the light source unit 20 can emit, as the illumination light, narrow-band (the wavelength range is in a range from about 10 nm to 20 nm) violet light, blue light, green light, and red light. More specifically, the light source unit 20 can emit, as the illumination light, narrow-band violet light whose center wavelength is about 400 nm, first narrow-band blue light whose center wavelength is about 450 nm, second narrow-band blue light whose center wavelength is about 470 nm, narrow-band green light whose center wavelength is about 540 nm, and narrow-band red light whose center wavelength is about 640 nm. Besides, the light source unit 20 can emit white light as the illumination light by combining the wide-band or narrow-band violet light, blue light, green light, and red light.

Note that for the light source unit 20, instead of the LEDs, a combination of a laser diode (LD), a fluorescent body, and a band limiting filter, a combination of a lamp such as a xenon lamp and a band limiting filter, and the like can be used. It is needless to say that the fluorescent body or the band limiting filter can be combined and used also in a case where the light source unit 20 is formed of LEDs.

The light source control unit 22 independently controls timings for turning on and off the respective light sources that constitute the light source unit 20, light emission amounts at the time of turning on, and the like. As a result, the light source unit 20 can emit the plurality of kinds of illumination light with different wavelengths. In addition, the light source control unit 22 controls the light source unit 20 in accordance with the timing (so-called frame) of an image sensor 48 for imaging.

Illumination light emitted from the light source unit 20 enters a light guide 41. The light guide 41 is incorporated in the endoscope 12 and a universal cord, and the illumination light propagates therethrough to the tip part 12*d* of the endoscope 12. The universal cord is a cord connecting the endoscope 12, the light source device 14, and the processor device 16. Note that a multi-mode fiber can be used as the light guide 41. As an example, a small-diameter fiber cable having a core diameter of 105 μm, a clad diameter of 125 μm, and a diameter of Ø 0.3 to 0.5 mm including a protective layer serving as an outer skin can be used. Note that nm represents nanometers, μm represents micrometers, and mm represents millimeters.

The tip part 12*d* of the endoscope 12 is provided with an illumination optical system 30*a* and an imaging optical system 30*b*. The illumination optical system 30*a* has an illumination lens 45, and an observation target is irradiated with illumination light through the illumination lens 45. The imaging optical system 30*b* has an objective lens 46, a zoom lens 47, and the image sensor 48. The image sensor 48 images the observation target by using, for example, reflected light (including, in addition to reflected light, scattered light, fluorescence emitted from the observation target, fluorescence caused by medicine that is, for example, administered to the observation target, and the like) of illumination light returning from the observation target through the objective lens 46 and the zoom lens 47. The zoom lens 47 is moved by operating the zoom operating unit 13 and zooms in or zooms out the observation target imaged by the image sensor 48.

The image sensor 48 is, for example, a color sensor having color filters of the primary color system and includes three types of pixels: a B pixel (blue pixel) having a blue color filter; a G pixel (green pixel) having a green color filter; and an R pixel (red pixel) having a red color filter. The blue color filter mainly transmits violet to blue light. The green color filter mainly transmits green light. The red color filter mainly transmits red light. When the observation target is imaged by using the image sensor 48 of the primary color system as described above, three types of images at most, which are a B image (blue image) from the B pixel, a G image (green image) from a G pixel, and an R image (red image) from the R pixel, can be obtained at the same time.

Note that a charge coupled device (CCD) sensor or a complementary metal oxide semiconductor (CMOS) sensor can be used as the image sensor 48. In addition, although the image sensor 48 according to this embodiment is a color sensor of the primary color system, a color sensor of the complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the pixels of the above respective colors when using the color sensor of the complementary color system can be converted into a B image, a G image, and an R image through complementary color-to-primary color conversion. In addition, instead of the color sensor, a monochrome sensor without a color filter can be used as the image sensor 48. In this case, by sequentially imaging the observation target by using illumination light of the respective colors such as BGR, images of the above respective colors can be obtained.

The processor device 16 has a control unit 52, an image acquiring unit 54, an image processing unit 61, and a display control unit 66.

The control unit 52 performs general control of the endoscope system 10 such as synchronization control of an illumination-light irradiation timing and an imaging timing. In addition, if the type, number, or the like of a region that is to be subjected to region determination is set by using the console 19 or the like, the control unit 52 inputs the setting to the light source control unit 22.

The image acquiring unit 54 acquires images obtained by imaging the observation target from the image sensor 48. In this embodiment, since the image sensor 48 has the color filters, the image acquiring unit 54 acquires images of respective colors of illumination light and of respective color filters. An image acquired by the image acquiring unit 54 from the image sensor 48 (image obtained by imaging) and a display image generated by using the image acquired by the image acquiring unit 54 from the image sensor 48 are each an "endoscope image". Hereinafter, unless explicitly distinguished, a simple term "image" means the endoscope image that is obtained by imaging the observation target and is acquired from the image sensor 48, and a simple term "endoscope image" means a display endoscope image 101 (see FIG. 6).

The image acquiring unit 54 has a digital signal processor (DSP) 56, a noise reduction unit 58, and a conversion unit 59, and performs various kinds of processing on the acquired images by using these units, as needed.

The DSP 56 performs various kinds of processing on the acquired images, such as defect correction processing, offset processing, gain correction processing, linear matrix processing, gamma conversion processing, demosaicing processing, and YC conversion processing, as needed.

The defect correction processing is processing for correcting the pixel value of a pixel corresponding to a defective pixel of the image sensor 48. The offset processing is processing for setting an accurate zero level by reducing a dark current component from an image subjected to the defect correction processing. The gain correction processing is processing for adjusting the signal level of each image by multiplying the image subjected to the offset processing by a gain. The linear matrix processing is processing for increasing the color reproducibility of an image subjected to the offset processing, and the gamma conversion processing is processing for adjusting the brightness and saturation of an image subjected to the linear matrix processing. The demosaicing processing (also referred to as isotropic processing or synchronization processing) is processing for interpolating the pixel value of a lacking pixel and is performed on an image subjected to the gamma conversion processing. The lacking pixel is a pixel without a pixel value due to the array of the color filters (because a pixel of another color is arranged in the image sensor 48). For example, since the B image is obtained by imaging the observation target by using the B pixel, there are no pixel values of pixels at positions corresponding to the G pixel and the R pixel. The demosaicing processing interpolates the B image and generates the pixel values of the pixels at positions corresponding to the G pixel and the R pixel in the image sensor 48. The YC conversion processing is processing for converting an image subjected to the demosaicing processing into a luminance channel Y, a chroma channel Cb, and a chroma channel Cr.

The noise reduction unit 58 performs noise reduction processing on the luminance channel Y, the chroma channel Cb, and the chroma channel Cr, by using, for example, a moving average method, a median filter method, or the like. The conversion unit 59 re-converts the luminance channel Y, the chroma channel Cb, and the chroma channel Cr, which have been subjected to the noise reduction processing, into images of BGR colors again.

The image processing unit 61 generates an endoscope image to be displayed on the monitor 18 by using the image acquired by the image acquiring unit 54. In addition, the image processing unit 61 calculates the index value by using the generated endoscope image. At this time, the image processing unit 61 identifies a region in which the index value cannot be accurately calculated and a region in which the index value can be accurately calculated, and calculates the index value in the region in which the index value can be accurately calculated.

Figure 3:
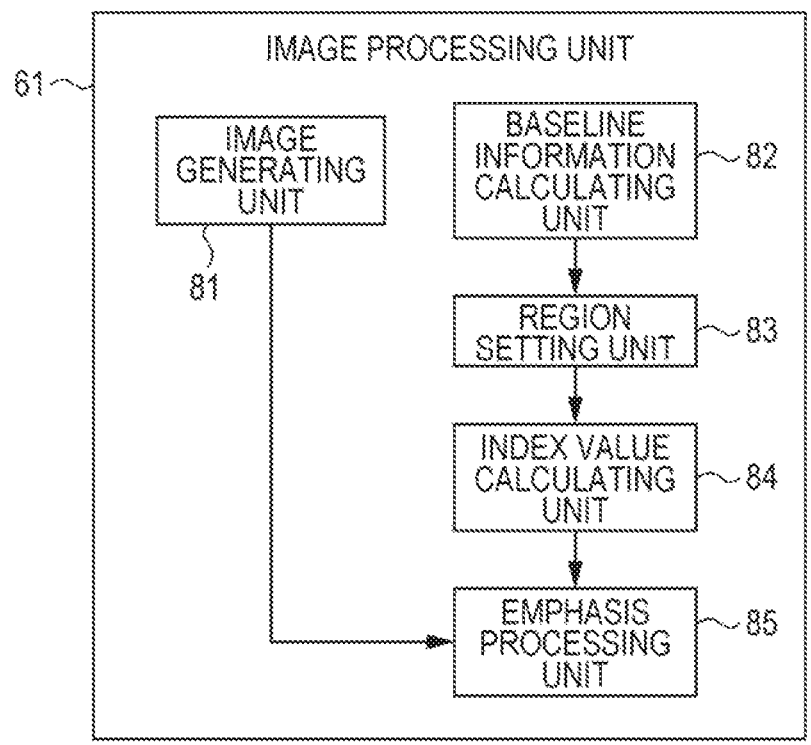
FIG. 3 is a block diagram of an image processing unit.

More specifically, as illustrated in FIG. 3, the image processing unit 61 includes an image generating unit 81, a baseline information calculating unit 82, a region setting unit 83, an index value calculating unit 84, and an emphasis processing unit 85.

The image generating unit 81 generates the display endoscope image 101 by using one or more images acquired by the image acquiring unit 54. When generating the display endoscope image 101, the image generating unit 81 performs, as needed, color conversion processing, hue emphasis processing, and structure emphasis processing on the images acquired by the image acquiring unit 54. In the color conversion processing, the images of BGR colors are subjected to 3×3 matrix processing, gradation transformation processing, three-dimensional look-up table (LUT) processing, and the like. The hue emphasis processing is processing for emphasizing the hue in an image, and the structure emphasis processing is, for example, processing for emphasizing a tissue or a structure of the observation target, such as a blood vessel or a pit pattern.

The baseline information calculating unit 82 calculates baseline information by using the endoscope image (image acquired by the image acquiring unit 54) obtained by imaging the observation target or the display endoscope image 101 generated by the image generating unit 81. The baseline information is information about light scattering characteristics or light absorbing characteristics of the observation target and is information that is at least not dependent on particular biological information. The term "not dependent" herein means at least a change of the baseline information being larger with respect to the magnitude of the light scattering characteristics or the light absorbing characteristics than with respect to the level of the particular biological information.

The "particular biological information" is, for example, information that changes due to the state of hemoglobin included in the observation target. Specifically, the particular biological information is an oxygen saturation, a hemoglobin concentration, a combination thereof, or the like. In addition, the "particular biological information" is, for example, information about a blood vessel included in the observation target. Specifically, the particular biological information is a blood vessel density, a blood vessel depth, a blood vessel thickness, a combination of two or more of these, or the like.

In this embodiment, the baseline information calculating unit 82 calculates the baseline information by using a plurality of images (endoscope images acquired from the image sensor 48) with different kinds of illumination light used for imaging. In addition, in this embodiment, the baseline information calculating unit 82 calculates baseline information that is at least not dependent on the oxygen saturation. Specifically, an image obtained by imaging the observation target by using the first narrow-band blue light is used as a B1 image, an image obtained by imaging the observation target by using the second narrow-band blue light is used as a B2 image, an image obtained by imaging the observation target by using the narrow-band green light is used as a G2 image, and an image obtained by imaging the observation target by using the narrow-band red light is used as an R2 image. Then, the baseline information calculating unit 82 calculates a ratio of the B1 image to the G2 image (hereinafter referred to as B1/G2), a ratio of the B2 image to the G2 image (hereinafter referred to as B2/G2), and a ratio of the R2 image to the G2 image (hereinafter referred to as R2/G2). Subsequently, an operation value "Z" is calculated according to Formula 1. A phase φ in Formula 1 is defined such that the operation value "Z" is constant with respect to the oxygen saturation of hemoglobin included in the observation target. The phase φ can be obtained in advance by experiment or the like.

$$Z = (B1/G2) \times \cos\varphi - (B2/G2) \times \sin\varphi \qquad \text{[Formula 1]}$$

Figure 4:
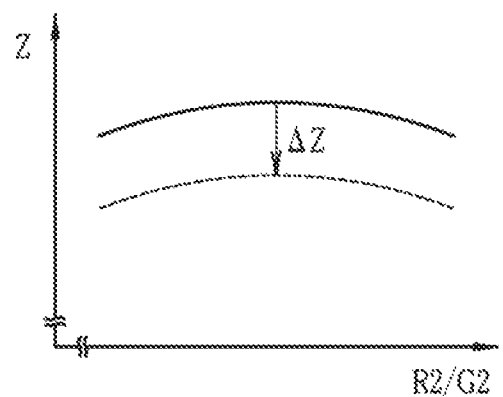
FIG. 4 is a graph illustrating an operation value "Z", which is baseline information.

If there is no residual liquid or the like including a yellow pigment such as bilirubin, as illustrated by the solid line in FIG. 4, the operation value "Z" becomes a fixed value in accordance with the value of the ratio R2/G2, not dependent on the oxygen saturation of the observation target. On the other hand, if there is a residual liquid or the like including a yellow pigment, as illustrated by the broken line, the operation value "Z" varies in accordance with the amount (density) of the yellow pigment included in the residual liquid or the like, although not dependent on the oxygen saturation of the observation target.

The operation value "Z" becomes the fixed value in accordance with the value of the ratio R2/G2 if there is no residual liquid or the like in a case where the observation target actually has light scattering characteristics or light absorbing characteristics that are expected in the calculation of the index value and in the adjustment of the phase φ. Thus, in a region in which the observation target actually has light scattering characteristics or light absorbing characteristics that are not expected in the calculation or the like of the index value, or a region in which the observation target seems to have the unexpected light scattering characteristics or light absorbing characteristics due to the way of irradiation with the illumination light or the like, the operation value "Z" also varies from the fixed value in accordance with the value of the ratio R2/G2 even if there is no residual liquid or the like. The region in which the observation target seems to have the unexpected light scattering characteristics or light absorbing characteristics due to the way of irradiation with the illumination light or the like is, for example, a dark region 102 (region that is darker than the other regions, see FIG. 6), a halation region (halation region in which the pixel value is saturated or nearly saturated and in which the observation target is difficult to observe, not illustrated), a region in which a treatment tool such as forceps is present (not illustrated), or the like. Also in a case where the operation value "Z" varies from the fixed value in accordance with the value of the ratio R2/G2 due to something other than the residual liquid or the like in this manner, as long as the phase $\varphi$ is appropriately adjusted, the operation value "Z" is not dependent on the oxygen saturation.

Thus, the operation value "Z" is "baseline information" that is information about the light scattering characteristics or the light absorbing characteristics of the observation target and that is at least not dependent on the oxygen saturation. Note that the baseline information calculating unit 82 calculates the operation value "Z", which is the baseline information, for each part composed of one or more pixels in an endoscope image. In this embodiment, the baseline information calculating unit 82 calculates the operation value "Z", which is the baseline information, for each pixel.

Although the value of the phase $\varphi$ is determined such that the baseline information is not dependent on the oxygen saturation in this embodiment, the phase $\varphi$ may alternatively be determined such that the baseline information is not dependent on the blood vessel density, the blood vessel depth, the blood vessel thickness, or the hemoglobin concentration. In this case, the baseline information calculating unit 82 can calculate the baseline information that is not dependent on the blood vessel density, the blood vessel depth, the blood vessel thickness, or the hemoglobin concentration. Similarly, in a case where the phase $\varphi$ is adjusted such that the base line information is not dependent on two or more pieces of the "particular biological information" from among the oxygen saturation, the blood vessel density, the blood vessel depth, the blood vessel thickness, and the hemoglobin concentration, the baseline information calculating unit 82 can calculate the baseline information that is not dependent on the two or more pieces of the "particular biological information".

Figure 7:
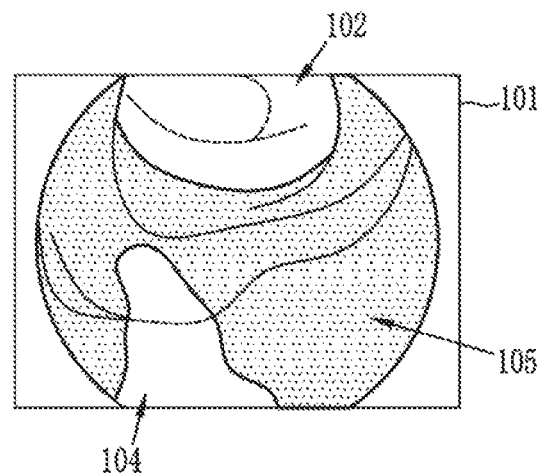
FIG. 7 is an explanatory diagram illustrating a calculation region in which an index value is to be calculated.
Figure 8:
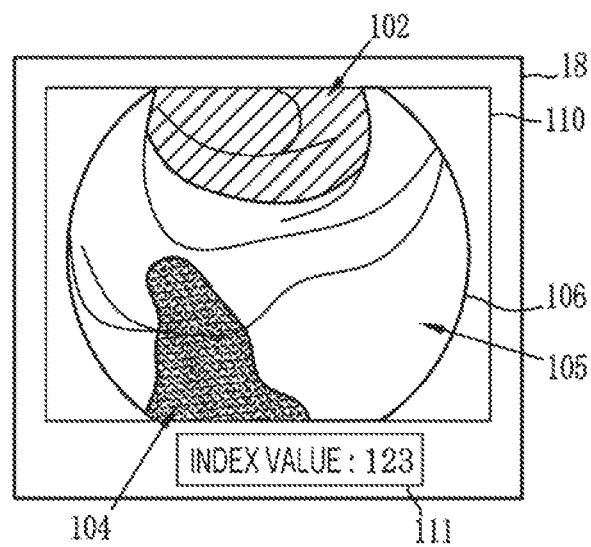
FIG. 8 is an example of display on a monitor.

By using the baseline information, the region setting unit 83 sets a calculation region 105 (also may be referred to as an index value calculation region, see FIG. 7 or FIG. 8) in which the index value representing the state of the observation target is to be calculated in an endoscope image. Specifically, if the light scattering characteristics and the light absorbing characteristics of the observation target are as expected in the calculation or the like of the index value and if there is no residual liquid or the like, with reference to a value $Z_0$ of the operation value "Z" in the actually calculated value of the ratio R2/G2, the region setting unit 83 calculates a change amount $\Delta Z$ ($=Z-Z_0$) of the actually calculated operation value "Z" in the actually calculated value of the ratio R2/G2 (see FIG. 4). The change amount $\Delta Z$ represents whether there is a residual liquid or the like and its amount or whether the light scattering characteristics and the light absorbing characteristics of the observation target are as expected in the calculation or the like of the index value.

Subsequently, the region setting unit 83, for example, compares the change amount $\Delta Z$ with a threshold value, and, as a result, identifies a region where the change amount $\Delta Z$ is larger than or equal to the threshold value and a region where the change amount $\Delta Z$ is less than the threshold value in the endoscope image. The region where the change amount $\Delta Z$ is larger than or equal to the threshold value is a region in which the index value cannot be accurately calculated because there is a residual liquid or the like or the light scattering characteristics or the light absorbing characteristics of the observation target do not fall within an expected range in the calculation of the index value. The region where the change amount $\Delta Z$ is less than the threshold value is a region in which the index value can be accurately calculated because there is no residual liquid or the like and the light scattering characteristics and the light absorbing characteristics of the observation target fall within an expected range in the calculation of the index value. Thus, in the endoscope image, the region setting unit 83 excludes the region where the change amount $\Delta Z$ is larger than or equal to the threshold value and, in the region where the change amount $\Delta Z$ is less than the threshold value, sets the calculation region 105 in which the index value is to be calculated. That is, by using the operation value "Z", which is the baseline information, by excluding the region in which the index value cannot be accurately calculated, such as a region 104 (see FIG. 6) in which a residual liquid or the like is present, the dark region 102, the halation region, a region in which a treatment tool is present, or the like, the region setting unit 83 sets the calculation region 105 in which the index value is to be calculated.

Note that the baseline information calculating unit 82 calculates the operation value "Z", which is the baseline information, for each part composed of one or more pixels in an endoscope image. Thus, for each part composed of one or more pixels for which the baseline information calculating unit 82 has calculated the operation value "Z", which is the baseline information, the region setting unit 83 calculates the change amount $\Delta Z$ and compares the change amount $\Delta Z$ with the threshold value to determine whether the index value is to be calculated for each part. As a result, the region setting unit 83 sets, as the calculation region 105 in which the index value is to be calculated, a region formed of the part composed of one or more pixels for which the baseline information calculating unit 82 has calculated the operation value "Z", which is the baseline information. In this embodiment, since the baseline information calculating unit 82 calculates the operation value "Z", which is the baseline information, for each pixel, the region setting unit 83 also calculates the change amount $\Delta Z$ and compares the change amount $\Delta Z$ with the threshold value for each pixel, and, as a result, sets whether the index value is to be calculated for each pixel.

By using the endoscope image, the index value calculating unit 84 calculates the index value in the region that is set as the calculation region 105 in which the region setting unit 83 calculates the index value. The index value calculating unit 84 can calculate, for example, the index value based on characteristics (e.g., size, shape, distribution, or density) of a structure that the observation target has, such as a pit pattern, or the index value based on characteristics of a tissue such as a blood vessel.

In this embodiment, the index value calculating unit 84 calculates the index value regarding a blood vessel (blood vessel index value). Specifically, the index value calculating unit 84 calculates blood vessel information or a blood vessel parameter as the index value (blood vessel index value). Examples of the blood vessel information include the number of blood vessels, number of branches, branch angle, distance between branches, the number of crossings, thickness, change in thickness, complexity of change in thickness, length, interval, depth with reference to a mucous membrane, difference in level, tilt, area, density, contrast, color, change in color, degree of tortuousness, hemoglobin concentration, oxygen saturation, artery ratio, vein ratio, concentration of an administered pigment, running pattern, blood amount, and the like. The blood vessel parameter is an operation result obtained by operation using two or more pieces of blood vessel information.

Note that the index value calculating unit 84 calculates the index value for each part composed of one or more pixels for which the baseline information calculating unit 82 has calculated the operation value "Z", which is the baseline information, or for each calculation region 105 in which the index value is to be calculated, which is set by the region setting unit 83. In this embodiment, the index value calculating unit 84 calculates the index value (blood vessel index value) for each calculation region 105 in which the index value is to be calculated, which is set by the region setting unit 83.

The emphasis processing unit 85 performs emphasis processing for emphasizing the region in which the index value has been calculated in the image acquired by the image acquiring unit 54 or the endoscope image generated by the image generating unit 81. Specifically, the emphasis processing unit 85 displays the outline of the region in which the index value has been calculated or performs frequency emphasis processing, edge emphasis processing, brightness adjustment processing, tone change processing, or the like on a part or all of the structure, tissue, or the like of the observation target within the region in which the index value has been calculated. Thus, the emphasis processing unit 85 emphasizes the region in which the index value has been calculated in the image acquired by the image acquiring unit 54 or the endoscope image generated by the image generating unit 81. In this embodiment, the emphasis processing unit 85 displays the outline of the region in which the index value has been calculated in the endoscope image generated by the image generating unit 81, so as to emphasize the region in which the index value has been calculated.

The display control unit 66 acquires the endoscope image on which the emphasis processing unit 85 has performed the emphasis processing or the endoscope image generated by the image generating unit 81 from the image processing unit 61, and converts the acquired endoscope image to a format that is suitable for display and outputs it to the monitor 18. Thus, the monitor 18 displays the endoscope image. In this embodiment, the display control unit 66 outputs the endoscope image on which the emphasis processing unit 85 has performed the emphasis processing to the monitor 18. As a result, the monitor 18, which is a display unit, displays the calculation region 105 in which the index value has been calculated in an emphasized manner in the endoscope image.

In addition, in accordance with settings or the like, the display control unit 66 outputs the index value or other additional information to the monitor 18. Thus, the monitor 18 displays the index value or the additional information in addition to the index value. In this embodiment, the display control unit 66 at least outputs the index value calculated by the index value calculating unit 84 to the monitor 18. As a result, the monitor 18, which is a display unit, displays the endoscope image and the index value calculated by the index value calculating unit 84.

Figure 5:
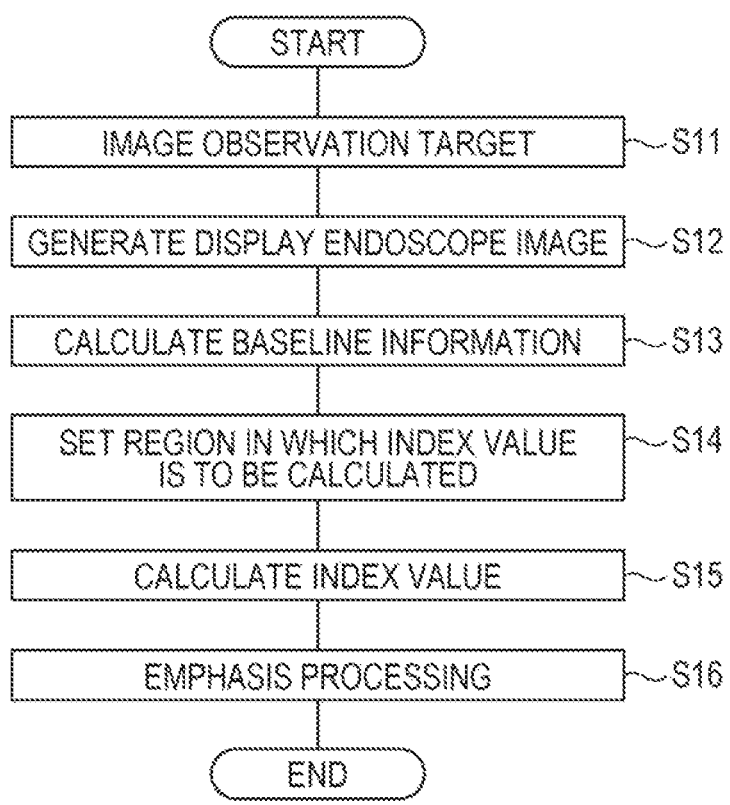
FIG. 5 is a flowchart illustrating the flow of operations of the endoscope system.

Next, the flow of operations of the endoscope system 10 will be described with reference to the flowchart illustrated in FIG. 5. Upon start of observation, the endoscope system 10 images the observation target while switching the illumination light as appropriate, and, as a result, the image acquiring unit 54 acquires images from the image sensor 48 (S11).

More specifically, the observation target is imaged while the illumination light is sequentially switched among first illumination light formed of the first narrow-band blue light, second illumination light formed of the second narrow-band blue light, the narrow-band green light, and the narrow-band red light, and third illumination light that is white light. A B1 image can be acquired through imaging using the first illumination light, and a B2 image, a G2 image, and an R2 image can be acquired through imaging using the second illumination light. Images of BGR colors can be acquired through imaging using the third illumination light, which is white light. Hereinafter, the images acquired from a B pixel, a G pixel, and an R pixel through imaging using the third illumination light, which is white light, will be referred to as a B3 image, a G3 image, and an R3 image, respectively.

Figure 6:
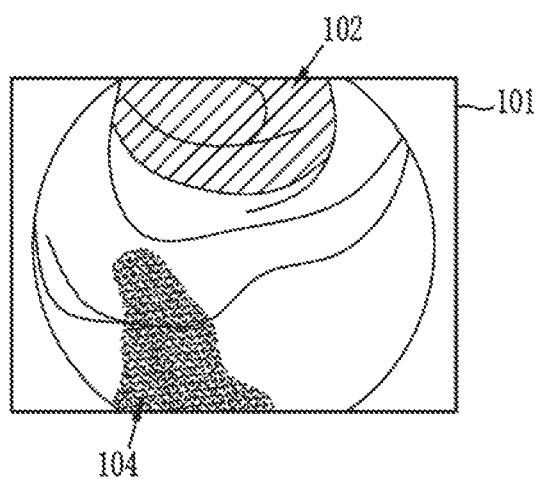
FIG. 6 is a display endoscope image.

Upon acquisition of the images of BGR colors in each frame of imaging as described above, the image generating unit 81 generates the display endoscope image 101 by using the B3 image, the G3 image, and the R3 image (S12). As illustrated in FIG. 6, in the display endoscope image 101, for example, the dark region 102 and the region 104 in which the residual liquid or the like is present are present.

On the other hand, upon acquisition of the images of BGR colors in each frame of imaging, the baseline information calculating unit 82 calculates the operation value "Z", which is the baseline information, by using the B1 image, the B2 image, and the G2 image (S13). Subsequently, on the basis of the change amount ΔZ from the reference value of the operation value "Z", which is the baseline information, the region setting unit 83 sets the calculation region 105 in which the index value is to be calculated. For example, in a case of the endoscope image 101, as illustrated in FIG. 7, the region setting unit 83 sets, as the calculation region 105 in which the index value is to be calculated, a region excluding the dark region 102 and the region 104 in which the residual liquid or the like is present.

Upon the region setting unit 83 setting the calculation region 105 in which the index value is to be calculated, the index value calculating unit 84 calculates the index value in the calculation region 105 (S15). For example, the index value calculating unit 84 extracts blood vessels by using the B1 image and the B2 image and calculates the blood vessel information of at least one of the extracted blood vessels as the index value (blood vessel index value).

Upon generation of the endoscope image 101 and calculation of the index value, the emphasis processing unit 85 performs emphasis processing on the endoscope image 101 (S16). Subsequently, the display control unit 66 outputs an endoscope image 110 after emphasis processing and the index value to the monitor 18. Thus, as illustrated in FIG. 8, the monitor 18 displays the endoscope image 110 after emphasis processing, displaying an outline 106 of the calculation region 105 in which the index value has been calculated in an emphasized manner, and also displays the index value that is calculated in the calculation region 105 within an index value display part 111.

In the above manner, the endoscope system 10 sets the calculation region 105 in which the index value is to be calculated, by using the baseline information (the operation value "Z"). Thus, it is possible to identify, more easily and more accurately than in the related art, the region in which the index value cannot be accurately calculated and the region in which the index value can be accurately calculated and to calculate the index value.

For example, in a case where the dark region 102 is identified on the basis of the brightness of pixels, and as a result, the dark region 102 is excluded from the calculation region 105 in which the index value is to be calculated, the region 104 with normal brightness, in which the residual liquid or the like is present, cannot be excluded from the calculation region 105 in which the index value is to be calculated. In contrast, in a case where the region 104 in which the residual liquid or the like is present is identified on the basis of the color of pixels, and as a result, the region 104 in which the residual liquid or the like is present is excluded from the calculation region 105 in which the index value is to be calculated, the dark region 102 that is not yellowish cannot be excluded from the calculation region 105 in which the index value is to be calculated. It is needless to say that the dark region 102 and the region 104 in which the residual liquid or the like is present may be identified and excluded individually. However, in reality, this process is possible but extremely heavy considering that it is necessary to exclude, in addition to these, the halation region and the region in which a treatment tool such as forceps is present from the calculation region 105 in which the index value is to be calculated.

In contrast, the endoscope system 10 can identify the region in which the index value cannot be accurately calculated, such as the dark region 102 and the region 104 in which the residual liquid or the like is present, and besides, the halation region, the region in which a treatment tool such as forceps is present, and the like, by the same method in accordance with a single reference, which is the baseline information, to set the calculation region 105 in which the index value is to be calculated. Thus, the endoscope system 10 can set the calculation region 105 in which the index value is to be calculated, more easily than the endoscope system of the related art.

In addition, in a case where the dark region 102 is identified and excluded from the calculation region 105 in which the index value is to be calculated, or in a case where the region 104 in which the residual liquid or the like is present is identified and excluded from the calculation region 105 in which the index value is to be calculated, for example, the light scattering characteristics or the light absorbing characteristics of the observation target are not typically considered. In contrast, in addition to the dark region 102, the region 104 in which the residual liquid or the like is present, the halation region, the region in which a treatment tool such as forceps is present, and the like, the endoscope system 10 can automatically exclude the region in which the index value cannot be accurately calculated, having unexpected light scattering characteristics or light absorbing characteristics. Thus, the endoscope system 10 can set the calculation region 105 in which the index value is to be calculated, more accurately than the endoscope system of the related art.

Note that the region setting unit 83 sets the calculation region 105 in which the index value is to be calculated, on the basis of the change amount ΔZ from the reference value of the operation value "Z", which is the baseline information, in the above embodiment. However, the region setting unit 83 can set the calculation region 105 in which the index value is to be calculated, on the basis of a comparison result of comparison between the operation value "Z", which is the baseline information, and the threshold value. In this case, as the threshold value, an upper limit threshold value and a lower limit threshold value are determined for at least each value of the ratio R2/G2. In this manner, substantially the same result as in the above embodiment, in which the calculation region 105 in which the index value is to be calculated is set on the basis of the change amount ΔZ, is obtained.

In addition, in a case where the region setting unit 83 sets the calculation region 105 in which the index value is to be calculated, on the basis of the comparison result of comparison between the operation value "Z", which is the baseline information, and the threshold value as described above, the threshold value used may change according to the image obtained through imaging or the property or the like of the endoscope image 101 (e.g., the way the observation target is imaged). For example, in a case of calculating a plurality of pieces of the baseline information, the threshold value can be set by using one piece of the baseline information selected from among the plurality of pieces of the baseline information or a statistic calculated by using the plurality of pieces of the baseline information. More specifically, as in the above embodiment, in a case where the baseline information calculating unit 82 calculates the operation value "Z", which is the baseline information, for each pixel, the region setting unit 83 can set a changeable threshold value with reference to a value (e.g., the operation value "Z" that is the closest to the median or the mode) selected from among the operation values "Z" for these pixels. In addition, the region setting unit 83 can calculate, by using the operation values "Z" calculated by the baseline information calculating unit 82 for the pixels, the average value, the median, the distribution, the mode, or the like (hereinafter referred to as a statistic) to set the changeable threshold value by using the calculated statistic. If the threshold value is set in the above manner, the calculation region 105 in which the index value is to be calculated can more accurately be set in some cases.

In the above embodiment, as a specific example, the calculation region 105 in which the index value is to be calculated is set by excluding the dark region 102 and the region 104 in which the residual liquid or the like is present. However, it is preferable that the region setting unit 83 set the calculation region 105 in which the index value is to be calculated by excluding at least one or more of the region 104 in which the residual liquid or the like is present, the dark region 102, the halation region, and the region in which a treatment tool is present, by using the baseline information. In this manner, among the region in which the residual liquid or the like is present, the dark region 102, the halation region, and the region in which a treatment tool is present, a region other than any one of regions that are explicitly set to be excluded can also be almost automatically excluded from the calculation region 105 in which the index value is to be calculated.

Note that an endoscope image for calculating the baseline information may differ from an endoscope image for calculating the index value depending on the type or the like of the index value to be calculated. Thus, in the above embodiment, the index value calculating unit 84 calculates the index value by using some endoscope images (the B1 image and the B2 image) among the plurality of endoscope images (the B1 image, the B2 image, and the G2 image) to be used for calculating the operation value "Z", which is the baseline information, by the baseline information calculating unit 82. However, the index value calculating unit 84 can calculate the index value by using one or more endoscope images with different kinds of illumination light used for imaging from the plurality of endoscope images to be used for calculating the baseline information by the baseline information calculating unit 82.

In the above embodiment, a hardware configuration of a processing unit that performs various kinds of processing is any of the following various processors. Various processors include a central processing unit (CPU) that is a general-purpose processor functioning as various processing units by executing software (programs), a programmable logic device (PLD) that is a processor in which the circuit configuration is changeable after manufacture, such as field programmable gate array (FPGA), a dedicated electric circuit that is a processor having a circuit configuration that is specially designed to execute specific processing, such as an application specific integrated circuit (ASIC), and the like.

One processing unit may be configured from one of these various processors, or may be configured from two or more processors of the same type or different types (e.g., a combination of a plurality of FPGAs or a combination of a CPU and an FPGA). In addition, a plurality of processing units may be configured from one processor.

Furthermore, the hardware configuration of these various processors is, more specifically, electric circuitry obtained by combining circuit devices such as semiconductor devices.

Figure 9:
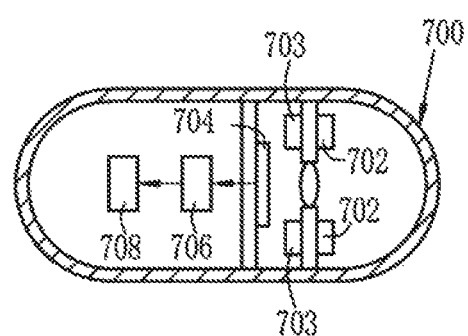
FIG. 9 is a schematic diagram of a capsule endoscope.

Although the present invention is implemented in the endoscope system 10 that performs observation by inserting the endoscope 12 provided with the image sensor 48 into a subject in the above embodiment, the present invention is also suitably used for a capsule endoscope system. As illustrated in FIG. 9, for example, the capsule endoscope system has at least a capsule endoscope 700 and a processor device (not illustrated).

The capsule endoscope 700 includes a light source unit 702, a control unit 703, an image sensor 704, an image processing unit 706, and a transmission/reception antenna 708. The light source unit 702 corresponds to the light source unit 20. The control unit 703 serves in the same manner as the light source control unit 22 and the control unit 52. In addition, the control unit 703 can wirelessly communicate with the processor device of the capsule endoscope system by using the transmission/reception antenna 708. The processor device of the capsule endoscope system is substantially the same as the processor device 16 according to the above embodiment, but the image processing unit 706 corresponding to the image acquiring unit 54 and the image processing unit 61 is provided in the capsule endoscope 700, and endoscope images are transmitted to the processor device through the transmission/reception antenna 708. The image sensor 704 is configured in the same manner as the image sensor 48.

REFERENCE SIGNS LIST

10 endoscope system
12 endoscope
12*a* insertion part
12*b* operating unit
12*c* bending part
12*d* tip part
12*e* angle knob
13 zoom operating unit
14 light source device
16 processor device
18 monitor
19 console
20, 702 light source unit
22 light source control unit
30*a* illumination optical system
30*b* imaging optical system
41 light guide
45 illumination lens
46 objective lens
47 zoom lens
48, 704 image sensor
52, 703 control unit
54, 706 image acquiring unit
56 digital signal processor (DSP)
58 noise reduction unit
59 conversion unit
61 image processing unit
66 display control unit
81 image generating unit
82 baseline information calculating unit
83 region setting unit
84 index value calculating unit
85 emphasis processing unit
101, 110 endoscope image
102 dark region
104 region in which residual liquid or the like is present
105 calculation region in which index value is to be calculated
106 outline
111 index value display part
700 capsule endoscope
708 transmission/reception antenna
Z operation value (baseline information)
ΔZ change amount
R2/G2 ratio of R2 image to G2 image

What is claimed is:

1. An endoscope system including a light source, an endoscope, and a processor device, the endoscope imaging an observation target irradiated with light emitted from the light source, the processor device performing system control and image processing, the endoscope system comprising:
  an image acquiring unit that acquires an endoscope image obtained by imaging the observation target;
  a baseline information calculating unit that calculates baseline information by using the endoscope image or a display endoscope image generated by using the endoscope image, the baseline information being information about light scattering characteristics or light absorbing characteristics of the observation target and information that is at least not dependent on particular biological information;
  a region setting unit that sets, by using the baseline information, a calculation region in which an index value is to be calculated, the index value indicating a state of the observation target; and
  an index value calculating unit that calculates the index value in the calculation region set by the region setting unit, by using the endoscope image or the display endoscope image generated by using the endoscope image,
  wherein the baseline information calculating unit calculates the baseline information by using a plurality of the endoscope images with different kinds of illumination light used for imaging.

2. The endoscope system according to claim 1,
wherein the baseline information calculating unit calculates the baseline information for each part composed of one or more pixels of the endoscope image, and
wherein the region setting unit determines whether the index value is to be calculated for the part to set a region formed of one or more of the parts as the calculation region in which the index value is to be calculated.

3. The endoscope system according to claim 1,
wherein the region setting unit sets the calculation region in which the index value is to be calculated, on the basis of a comparison result of comparison between the baseline information and a threshold value.

4. The endoscope system according to claim 2,
wherein the region setting unit sets the calculation region in which the index value is to be calculated, on the basis of a comparison result of comparison between the baseline information and a threshold value.

5. The endoscope system according to claim 3,
wherein, in a case where a plurality of pieces of the baseline information are calculated, the region setting unit sets the threshold value by using one piece of the baseline information among the plurality of pieces of the baseline information or a statistic calculated by using the plurality of pieces of the baseline information.

6. The endoscope system according to claim 4,
wherein, in a case where a plurality of pieces of the baseline information are calculated, the region setting unit sets the threshold value by using one piece of the baseline information among the plurality of pieces of the baseline information or a statistic calculated by using the plurality of pieces of the baseline information.

7. The endoscope system according to claim 1,
wherein the region setting unit excludes, by using the baseline information, any one or more of a region in which a residue or a residual liquid is present, a dark region, a halation region, or a region in which a treatment tool is present to set the calculation region in which the index value is to be calculated.

8. The endoscope system according to claim 2,
wherein the region setting unit excludes, by using the baseline information, any one or more of a region in which a residue or a residual liquid is present, a dark region, a halation region, or a region in which a treatment tool is present to set the calculation region in which the index value is to be calculated.

9. The endoscope system according to claim 3,
wherein the region setting unit excludes, by using the baseline information, any one or more of a region in which a residue or a residual liquid is present, a dark region, a halation region, or a region in which a treatment tool is present to set the calculation region in which the index value is to be calculated.

10. The endoscope system according to claim 4,
wherein the region setting unit excludes, by using the baseline information, any one or more of a region in which a residue or a residual liquid is present, a dark region, a halation region, or a region in which a treatment tool is present to set the calculation region in which the index value is to be calculated.

11. The endoscope system according to claim 5,
wherein the region setting unit excludes, by using the baseline information, any one or more of a region in which a residue or a residual liquid is present, a dark region, a halation region, or a region in which a treatment tool is present to set the calculation region in which the index value is to be calculated.

12. The endoscope system according to claim 1,
wherein the index value calculating unit calculates the index value by using one or more of the endoscope images for which kinds of illumination light used for imaging are different from kinds of illumination light for a plurality of the endoscope images to be used for calculating the baseline information by the baseline information calculating unit.

13. The endoscope system according to claim 1, further comprising:
a display unit that displays the endoscope image or an image generated by using the endoscope image, and the index value.

14. The endoscope system according to claim 1, further comprising:
a display unit that displays the calculation region in which the index value is to be calculated in the endoscope image or the image generated by using the endoscope image.

15. The endoscope system according to claim 1,
wherein the particular biological information is information that changes due to a state of hemoglobin included in the observation target.

16. The endoscope system according to claim 15,
wherein the particular biological information is an oxygen saturation or a hemoglobin concentration.

17. The endoscope system according to claim 1,
wherein the particular biological information is information about a blood vessel included in the observation target.

18. The endoscope system according to claim 17,
wherein the particular biological information is a blood vessel density, a blood vessel depth, or a blood vessel thickness.

19. A processor device that performs system control and image processing of an endoscope system having a light source and an endoscope that images an observation target irradiated with light emitted from the light source, the processor device comprising:
an image acquiring unit that acquires an endoscope image obtained by imaging the observation target;
a baseline information calculating unit that calculates baseline information by using the endoscope image or a display endoscope image generated by using the endoscope image, the baseline information being information about light scattering characteristics or light absorbing characteristics of the observation target and information that is at least not dependent on particular biological information;
a region setting unit that sets, by using the baseline information, a calculation region in which an index value is to be calculated, the index value indicating a state of the observation target; and
an index value calculating unit that calculates the index value in the calculation region set by the region setting unit, by using the endoscope image or the display endoscope image generated by using the endoscope image,
wherein the baseline information calculating unit calculates the baseline information by using a plurality of the endoscope images with different kinds of illumination light used for imaging.

20. A method for operating an endoscope system including a light source, an endoscope, and a processor device, the endoscope imaging an observation target irradiated with light emitted from the light source, the processor device performing system control and image processing, the method comprising:
- a step of acquiring, by an image acquiring unit, an endoscope image obtained by imaging the observation target;
- a step of calculating, by a baseline information calculating unit, baseline information by using the endoscope image or a display endoscope image generated by using the endoscope image, the baseline information being information about light scattering characteristics or light absorbing characteristics of the observation target and information that is at least not dependent on particular biological information;
- a step of setting, by a region setting unit by using the baseline information, a calculation region in which an index value is to be calculated, the index value indicating a state of the observation target; and
- a step of calculating, by an index value calculating unit, the index value in the calculation region set by the region setting unit, by using the endoscope image or the display endoscope image generated by using the endoscope image,
- wherein in the step of calculating, the baseline information is calculated by using a plurality of the endoscope images with different kinds of illumination light used for imaging.

* * * * *